United States Patent
Fliegel et al.

(10) Patent No.: US 10,460,924 B2
(45) Date of Patent: Oct. 29, 2019

(54) PROCESS FOR PRODUCING A GALLIUM ARSENIDE SUBSTRATE WHICH INCLUDES MARANGONI DRYING

(71) Applicant: FREIBERGER COMPOUND MATERIALS GMBH, Freiberg (DE)

(72) Inventors: Wolfram Fliegel, Dresden (DE); Christoph Klement, Chemnitz (DE); Christa Willnauer, Dorfhain (DE); Max Scheffer-Czygan, Chemnitz (DE); André Kleinwechter, Freiberg (DE); Stefan Eichler, Dresden (DE); Berndt Weinert, Freiberg (DE); Michael Mäder, Coswig (DE)

(73) Assignee: FREIBERGER COMPOUND MATERIALS GMBH, Freiberg (DE)

( * ) Notice: Subject to any disclaimer, the term of this patent is extended or adjusted under 35 U.S.C. 154(b) by 292 days.

(21) Appl. No.: 14/767,603

(22) PCT Filed: Feb. 12, 2014

(86) PCT No.: PCT/EP2014/052745
§ 371 (c)(1),
(2) Date: Aug. 13, 2015

(87) PCT Pub. No.: WO2014/124980
PCT Pub. Date: Aug. 21, 2014

(65) Prior Publication Data
US 2015/0371844 A1    Dec. 24, 2015

(30) Foreign Application Priority Data

Feb. 15, 2013    (DE) .................. 10 2013 002 637

(51) Int. Cl.
*C30B 33/10*    (2006.01)
*H01L 21/02*    (2006.01)
(Continued)

(52) U.S. Cl.
CPC ...... *H01L 21/02054* (2013.01); *G01N 21/211* (2013.01); *H01L 21/02046* (2013.01);
(Continued)

(58) Field of Classification Search
CPC .. C30B 9/00; C30B 9/04; C30B 11/00; C30B 11/006; C30B 25/00; C30B 25/02;
(Continued)

(56) References Cited

U.S. PATENT DOCUMENTS

| 4,738,935 A | 4/1988 | Shimbo et al. |
| 6,230,720 B1 * | 5/2001 | Yalamanchili .... H01L 21/02052 134/1.3 |

(Continued)

FOREIGN PATENT DOCUMENTS

| CN | 1787178 | 6/2006 |
| CN | 101315910 | 12/2008 |

(Continued)

OTHER PUBLICATIONS

Tanimoto, et al. publication entitled "Reduction of schottky reverse leakage current using GaAs surface cleaning with UVO3 treatment," Japanese Journal of Applied Physics, vol. 38, pp. 3982-3985 (1999).*

(Continued)

*Primary Examiner* — Kenneth A Bratland, Jr.
(74) *Attorney, Agent, or Firm* — A.C. Entis-IP Ltd.; Allan C. Entis; Kenichi N. Hartman

(57) ABSTRACT

The present invention relates to a novel process for producing a surface-treated gallium arsenide substrate as well as novel provided gallium arsenide substrates as such as well as the use thereof. The improvement of the process according to the invention is based on a particular final surface treatment with an oxidation treatment of at least one surface of the gallium arsenide substrate in dry condition by means (Continued)

of UV radiation and/or ozone gas, a contacting of the at least one surface of the gallium arsenide substrate with at least one liquid medium and a Marangoni drying of the gallium arsenide substrate. The gallium arsenide substrates provided according to the invention exhibit a so far not obtained surface quality, in particular a homogeneity of surface properties, which is detectable by means of optical surface analyzers, specifically by means of ellipsometric lateral substrate mapping for the optical contact-free quantitative characterization.

10 Claims, 10 Drawing Sheets

(51) Int. Cl.
  *G01N 21/21* (2006.01)
  *H01L 29/20* (2006.01)
  *G01N 21/17* (2006.01)

(52) U.S. Cl.
  CPC .. *H01L 21/02052* (2013.01); *H01L 21/02395* (2013.01); *H01L 29/20* (2013.01); *G01N 2021/178* (2013.01); *Y10T 428/24355* (2015.01)

(58) Field of Classification Search
  CPC ....... C30B 25/16; C30B 25/18; C30B 25/186; C30B 29/00; C30B 29/10; C30B 29/40; C30B 29/42; C30B 33/00; C30B 33/08; C30B 33/10; C30B 33/12; H01L 21/02054; H01L 21/02046; H01L 21/02052; H01L 21/02395; H01L 29/20; G01N 21/211; G01N 2021/178; Y10T 428/24355
  USPC ....... 117/73, 76–78, 80–85, 88, 94, 97, 106, 117/937, 953–954
  See application file for complete search history.

(56) References Cited

U.S. PATENT DOCUMENTS

| | | | |
|---|---|---|---|
| 2001/0014570 A1* | 8/2001 | Wenski | B24B 9/065 451/41 |
| 2004/0058626 A1* | 3/2004 | Filipozzi | B24B 37/0056 451/57 |
| 2005/0139231 A1* | 6/2005 | Abadie | B08B 3/08 134/2 |
| 2006/0264011 A1 | 11/2006 | Hachigo et al. | |
| 2007/0269989 A1* | 11/2007 | Nishiura | H01L 21/02008 438/718 |
| 2008/0274626 A1 | 11/2008 | Glowacki et al. | |
| 2008/0292877 A1* | 11/2008 | Horie | H01L 21/02052 428/336 |
| 2009/0291567 A1 | 11/2009 | Hachigo et al. | |

FOREIGN PATENT DOCUMENTS

| | | |
|---|---|---|
| CN | 101452894 | 6/2009 |
| CN | 101501474 | 8/2009 |
| EP | 1724821 | 11/2006 |
| JP | 07211688 | 8/1995 |
| JP | 09-320967 | 12/1997 |
| JP | 10-012577 | 1/1998 |
| JP | 11-204471 | * 1/1998 |
| JP | 11204471 | 7/1999 |
| JP | 2006352075 | 12/2006 |
| JP | 2009182135 | 8/2009 |
| WO | 2006001117 | 4/2008 |

OTHER PUBLICATIONS

Wolke, et al. publication entitled "Marangoni wafer drying avoids disadvantages," Solid State Technology, vol. 39, pp. 87-90 (1986).*
Tanimoto, et al. publication entitled "Reduction of schottky reverse leakage current using GaAs surface cleaning with UVO3 treatment," Japanese Journal of Applied Physics, vol. 38, pp. 3982-3985 (1999). (Year: 1999).*
Wolke, et al. publication entitled "Marangoni wafer drying avoids disadvantages," Solid State Technology, vol. 39, pp. 87-90 (1986). (Year: 1986).*
Technical Brochure: Optical Surface Analyser Candela CS20, KLA Tencor, 2010.
EP Office Action dated Jun. 30, 2016 for corresponding application No. 14705102.3.
Chinese Office Action dated Mar. 24, 2017 for corresponding application No. 201480004737.9.
Tanimoto T et al, "Reduction of Schottky reverse leakage current using GaAs surface cleaning with UV-03 treatment", Japanese Journal of Applied Physics, vol. 38, Jul. 1999, pp. 3982-3985.
Wolke K et al, "Marangoni Wafer Drying Avoids Disadvantages", Solid State Technology, Pennwell Corporation, Tulsa, OK, USA, vol. 39, Aug. 1, 1996, pp. 87-90.
Allwood D A et al, Monitoring epiready semiconductor wafers, thin solid films 412, 2002, pp. 76-83.
Bechtler Laurie et al., Optical surface analysis: a new technique for the inspection and metrology of optoelectronic films and wafers, Integrated Optical Devices: Fabrication and Testing, 109, Abstract, Apr. 7 2003, From Conference vol. 4944.
Bünger Th et al, Development of a vertical gradient freeze process for low EPD GaAs substrates, Materials Science and Engineering B, 80(19), 2001, pp. 5-9.
Burkeen Frank, Emerging Standardization for Sapphire Substrate Inspection, Time-to-Yield, KLA-Tencor Corporation 2008, p. 3.
Flade T et al, State of the art 6" Si GaAs wafers made of conventionally grown LEC-crystals, Journal of Crystal Growth 198/199, 1999, pp. 336-342.
Govaerts, Paul et al, Box and whisker plots for graphic presentation of audiometric results of conductive hearing loss treatment, Otolaryngol Head Neck Surg 1998; 118, pp. 892-895.
Moré Jorge J, Lecture Notes in Mathematics, The Levenberg-Marquardt Algorithm: Implementation and Theory, 1978, pp. 105-116.
Schoonjans F et al, Estimation of Population Percentiles, Lippincott Williams & Wilkins, Epidemiology, vol. 22, No. 5, Sep. 2011, pp. 750-751+ Appendix.
Schröder-Oeynhausen F et al, Depth Analysis of GaAs-Oxide Layers with SIMS, e-Beam SNMS and ARXPS, Wiley, 1997, pp. 351-354.
Song J S et al, Wet chemical cleaning process of GaAs substrate for ready-to-use, Journal of Crystal Growth 264, 2004, pp. 98-103.
Surdu-Bob C C et al, An X-ray photoelectron spectroscopy study of the oxides of GaAs, Applied Surface Science 183, 2001, pp. 126-136.
Tukey John W, Exploratory Data Analysis, Addison-Wesley Series in Behavioral Science: Quantitative Methods, 1977, pp. 38-42.
International Search Report dated Oct. 24, 2014 for International Application No. PCT/EP2014/52745 filed Feb. 12, 2014.
Taiwanese Office Action dated Feb. 14, 2017 for corresponding application No. 103104814.
Office Action dated Nov. 7, 2017 for corresponding Japanese application No. 2015-557415.
Seah et al., Ultrathin SiO2 on Si: III Mapping the layer thickness efficiently by XPS+, Surface and Interface Analysis, 2002, 33, pp. 960-963.
European Office Action dated Oct. 31, 2018 for corresponding application No. 18156119.2 filed Feb. 12, 2014.
Chinese Office Action dated Mar. 19, 2019 for corresponding application No. 20148004737.9.

* cited by examiner

Comparative Example 1　　Example 1　　Example 2

Comparative	Example 1	Example 2
Example 1

Comparative Example 1　　Example 1　　Example 2

PROCESS FOR PRODUCING A GALLIUM ARSENIDE SUBSTRATE WHICH INCLUDES MARANGONI DRYING

RELATED APPLICATIONS

The present application is a U.S. National Phase of PCT/EP2014/052745 filed on Feb. 12, 2014, which claims the benefit under 35 U.S.C 119(a)-(d) from German application 10 2013 002 637.7 filed on Feb. 15, 2013. The contents and disclosures of these prior applications are incorporated herein by reference in their entirety.

The present invention relates to a process for producing a surface-treated gallium arsenide substrate as well as a gallium arsenide substrate as such and the use thereof.

BACKGROUND OF THE INVENTION

Gallium arsenide substrate wafers are used for the production of high-frequency amplifiers and switches as well as light-emitting components such as semiconductor lasers and luminescence diodes. The component structures (transistors and diodes) are typically produced from epitaxially deposited mixed crystal stacks of variable elements which can be selected from the group of Ga—In—As—P—Al—N, wherein in the individual layers different electronic properties can be set at same crystal lattice parameters by specific compositions. This kind of lattice-adapted epitaxy aims at a very high layer quality and low defect densities. In this regard the layer quality depends not only on the conditions in the epitaxy process, but it is also influenced by the substrate properties.

The production of GaAs substrates starts with the growing of respective bulk crystals and the subsequent singularization in a sawing/separating process (see for example T. Flade et al., "State of the art 6" SI GaAs wafers made of conventionally grown LEC-crystals", Journal of Crystal Growth, 198-199(1), 1999, p. 336-342 and Th. Bünger et al., "Development of a vertical gradient freeze process for low EPD GaAs substrates", Materials Science and Engineering B, 80(1), 2001, p. 5-9). Subsequently the substrates are treated in a multi-stage process, inter alia polished, in order to obtain advantageous properties of geometry (thickness, curvature, wedge shape) and roughness (see for example Flade et al.). After the last polishing step the pure highly reactive GaAs surface is exposed, and an oxide growth inevitably starts immediately. The typical subsequent cleaning in liquid media entails a sequence of oxide forming and respectively oxide removing steps and primarily serves to decrease the number of particles and of residual impurities or respectively residual contaminations on the substrate. During the last cleaning steps and the subsequent drying of the substrate an oxide layer is formed. This oxide layer can still undergo change during the time until the insertion of the substrates into the epitaxy apparatus (see for example D. A. Allwood, S. Cox, N. J. Mason, R. Palmer, R. Young, P. J. Walker, Thin Solid Films, 412, 2002, p. 76-83).

The composition of the oxide layer can be measured for example by means of X-ray-excited photoelectron spectroscopy (XPS) in which core electrons of the oxidized atom are spectroscopically investigated. The oxidation states can be determined from the energetic shifts of the excited electrons. The measurement methodology is described for the example of GaAs in detail in C. C. Surdu-Bob, S. O. Saied, J. L Sullivan, Applied Surface Science, Volume 183(1-2), 2001, p. 126-136. Depending on the oxidation conditions the ratio of arsenic and gallium oxides lies between 1 and 5. Typically $GaO$, $Ga_2O_3$ and $As_2O$, $AsO$, $As_2O_3$, $As_2O_5$ occur (see for example F. Schröder-Oeynhausen, "Oberflächenanalytische Charakterisierung von metallischen Verunreinigungen and Oxiden auf GaAs", Dissertation, University of Münster, 1996 and J. S. Song, Y. C. Choi, S. H. Seo, D. C. Oh, M. W. Cho, T. Yao, M. H. Oh, Journal of Crystal Growth, 264, 2004, p. 98-103).

In order to influence the growth of epitaxial layers also by the surface properties of the wafer surface, so far the possibility for the later thermal desorption of surface layers (e.g. oxides) immediately before the start of the epitaxial processes in the epitaxy apparatus was frequently used. In this respect the roughness of a thermally desorbed surface, the degree of contaminations and impurities (particles) play a role in the qualitative properties of the layer stacks to be deposited and the components produced therefrom. For III/V semiconductors the dependence of the quality of epitaxially deposited layers on parameters of the processes used for the preceding cleaning and surface properties associated therewith were investigated. In this regard it was putatively presumed that the wet chemical treatment on the whole surface of the wafer is homogenous in each of the steps.

The wet chemical cleaning of wafers is typically performed in successive liquid baths. Process racks with wafers are usually set from bath to bath by means of automatic transport systems and finally dried. In most cases the cleaning comprises a sequence of acidic and alkaline wet steps with intermediate rinsing steps in deionized water (DI water). In this respect ammonium hydroxide ($NH_4OH$) or organic amines are usually used as alkaline components. Acids used are for example hydrogen fluoride (HF) and hydrogen chloride (HCl), further also sulfuric acid ($H_2SO_4$) or organic acids. Often the cleaning media additionally contain additives such as for example oxidizing agents, surfactants (surface-active agents) or chelating agents. For the removal of particles for example ultrasound or megasound in individual baths is used. For the drying of wafers rinsed with DI water in principle diverse processes are conceivable, in practice the drying conventionally relies on the removal of the DI water using the centrifugal forces during the rapid rotation of the wafers or respectively wafer carriers (spin drying) (see e.g. Song et al.).

However, the conventional processes do not provide gallium arsenide substrates which fulfill the increasing requirements on subsequent epitaxy processes in that the large-area and reliable epitaxial production of components with the needed layer quality and the required defect densities in appropriate yield is to be enabled.

The object of the present invention is to provide an improved process for the production of gallium arsenide substrates exhibiting favorable properties for a subsequent epitaxy.

SUMMARY OF THE INVENTION

For the characterization of the surface properties of differently treated gallium arsenide substrates the ellipsometric lateral substrate mappings of an optical surface analyzer were used. Details of the measurement method and the analysis methods used are given in the description of the preferred embodiments as well as in the description of the Examples.

Without limiting the invention, in the following items are provided describing main aspects, preferred embodiments and particular features of the present invention:

1) A process for producing a surface-treated gallium arsenide substrate, the process comprising the steps:
   a) providing a gallium arsenide substrate;
   b) oxidation treatment of at least one surface of the gallium arsenide substrate in dry condition by means of UV radiation and/or ozone gas;
   c) contacting the at least one surface of the gallium arsenide substrate with at least one liquid medium; and
   d) Marangoni drying of the gallium arsenide substrate.
2) The process according to item 1, wherein step c) comprises the following steps:
   i) contacting the at least one surface of the gallium arsenide substrate with alkaline aqueous solution, optionally applying megasound; and
   ii) subsequently contacting the at least one surface of the gallium arsenide substrate with water.
3) The process according to item 1 or 2, wherein in step c) an alkaline aqueous solution is used which is a solution of $NH_3$ or organic amine in water, preferably of $NH_3$, more preferably of $NH_3$ in a concentration of 0.1-2 percent by volume and particularly preferably of $NH_3$ in a concentration of 0.2-1 percent by volume.
4) The process according to item 2 or 3, wherein step c) further comprises the following steps:
   iii) subsequent to step ii) contacting the at least one surface of the gallium arsenide substrate with acidic aqueous solution, optionally in the presence of an oxidizing agent; and
   iv) subsequently further contacting the at least one surface of the gallium arsenide substrate with water, wherein preferably the water at least initially contains a pH value modifying additive.
5) The process according to item 4, wherein the acidic aqueous solution is a solution of HCl or HF in water, preferably in a concentration of 0.1-0.5 percent by volume, more preferably in a concentration of 0.1-0.25 percent by volume and particularly preferably is HCl in a concentration of 0.15-0.25 percent by volume.
6) The process according to item 4 or 5, wherein the oxidizing agent in the acidic aqueous solution is ozone or $H_2O_2$, preferably ozone, more preferably ozone in a concentration of 10-50 ppm and particularly preferably ozone in a concentration of 30-50 ppm.
7) The process according to one of the items 4-6, wherein the pH value modifying additive is basic or acidic, preferably basic, more preferably $NH_3$, even more preferably $NH_3$ in a concentration of 0.01-0.2 percent by volume and particularly preferably $NH_3$ in a concentration of 0.05-0.1 percent by volume.
8) The process according to one of the items 4-7, wherein in step c) subsequent to step iv) further steps according to the steps i) and ii) are carried out.
9) The process according to one of the items 2-8, wherein water is deionized water or ultra-pure water.
10) The process according to one of the preceding items, wherein the gallium arsenide substrate provided in step a) was beforehand singularized or respectively separated from a gallium arsenide bulk crystal and/or was polished and preferably pre-cleaned, more preferably wet chemically pre-cleaned and particularly preferably pre-cleaned wet chemically and with brush scrubbing.
11) The process according to one of the preceding items, wherein the gallium arsenide substrate provided in step a) is doped or undoped.
12) The process according to one of the preceding items, wherein in step d) an aqueous isopropanol solution is used.
13) A process for producing a plurality of surface-treated gallium arsenide substrates, wherein in the process according to one of the preceding items a plurality of gallium arsenide substrates is simultaneously subjected to the respective steps b)-d).
14) A gallium arsenide substrate which exhibits at least one surface having in ellipsometric lateral substrate mapping with an optical surface analyzer a variation of the laterally resolved background-corrected measurement signal whose distribution percentile of 1% normalized to the substrate average of the phase shift signal is greater than −0.0065.
15) The gallium arsenide substrate according to item 14, which exhibits at least one surface having in ellipsometric lateral substrate mapping with an optical surface analyzer a variation of the laterally resolved background-corrected measurement signal whose distribution percentile of 1% normalized to the substrate average of the phase shift signal is greater than −0.0060, preferably greater than −0.0055, more preferably greater than −0.0050, even more preferably greater than −0.0045, particularly preferably greater than −0.0040, particularly greater than −0.0030, in particular greater than −0.0020, even greater than −0.0010 and up to 0.0000 excluding 0.0000.
16) A gallium arsenide substrate which exhibits at least one surface having in ellipsometric lateral substrate mapping with an optical surface analyzer, based on a substrate diameter of 150 mm as reference, a defect number of <6000 and/or a total defect area of less than 2 $cm^2$, wherein a defect is defined as a continuous area greater than 1000 $\mu m^2$ having a deviation from the average measurement signal in ellipsometric lateral substrate mapping with an optical surface analyzer of at least ±0.05%.
17) The gallium arsenide substrate according to item 16, wherein the defect number is <5000, preferably <4000, more preferably <3000, even more preferably <2000, yet more preferably <1000, still more preferably <500, still more preferably <300, still more preferably <250, still more preferably <200, still more preferably <150 and particularly preferably <100, and/or
the total defect area is less than 1 $cm^2$, preferably less than 0.5 $cm^2$, even more preferably less than 0.1 $cm^2$, even more preferably less than 0.05 $cm^2$, still more preferably less than 0.01 $cm^2$, still more preferably less than 0.005 $cm^2$ and particularly preferably less than 0.0035 $cm^2$.
18) A gallium arsenide substrate which is produced according to the process according to one of the items 1-12.
19) The gallium arsenide substrate according to one of the items 14-18, wherein the diameter is at least 100 mm, preferably at least 150 mm and more preferably at least 200 mm.
20) A polished and surface-finished gallium arsenide substrate having a diameter of at least 150 mm, wherein the surface treatment comprises an oxidation treatment of at least one surface of the gallium arsenide substrate in dry condition by means of UV radiation and/or ozone gas, a contacting of the at least one surface of the gallium arsenide substrate with at least one liquid medium and a Marangoni drying of the gallium arsenide substrate.
21) The gallium arsenide substrate according to item 20, having a thickness of not greater than approximately 600 $\mu m$ or respectively not less than approximately 800 $\mu m$.
22) The gallium arsenide substrate according to item 20 or 21, wherein the thickness lies in a range from approximately 100 to approximately 600 $\mu m$ or respectively the thickness is greater than approximately 800 $\mu m$ and the thickness preferably lies in a range from approximately 250 to approximately 500 μm or respectively from approximately 800 to approximately 2000 μm.

23) A polished and surface-finished gallium arsenide substrate, exhibiting a thickness of not greater than approximately 600 μm.

24) A polished and surface-finished gallium arsenide substrate having a thickness of not less than approximately 800 μm.

25) The polished and surface-finished gallium arsenide substrate according to one of the items 20 to 24, wherein the treated surface of the substrate exhibits the properties defined in one of the items 14 to 17.

26) The gallium arsenide substrate according to one of the items 14-25, wherein said gallium arsenide substrate is doped or undoped.

27) A gallium arsenide substrate which exhibits at least one surface having within 9 months, preferably 12 months, after the production a substantially not deteriorating, preferably a not deteriorating, variation of the laterally resolved background-corrected measurement signal in ellipsometric lateral substrate mapping with an optical surface analyzer.

28) The gallium arsenide substrate according to one of the items 14-26, wherein the at least one surface within six months after the production exhibits a substantially not deteriorating, preferably a not deteriorating, variation of the laterally resolved background-corrected measurement signal in ellipsometric lateral substrate mapping with an optical surface analyzer.

29) A plurality of gallium arsenide substrates, which are produced according to the process according to one of the items 1-13 and exhibit among one another a substantially same, preferably same, variation from substrate to substrate of the laterally resolved background-corrected measurement signal in ellipsometric lateral substrate mapping of the respective at least one surface with an optical surface analyzer.

30) The gallium arsenide substrate according to one of the items 14 to 17 and 25 to 28 or respectively the plurality of gallium arsenide substrates according to item 29, wherein ellipsometric lateral substrate mapping with an optical surface analyzer is carried out with an optical surface analyzer analogous to Candela CS20, preferably specifically with an optical surface analyzer Candela CS20, more preferably with an optical surface analyzer using laser light having a wavelength of 405 nm and whose optical path comprises a half-wave plate, a quarter-wave plate, a polarization-sensitive beam splitter and two detectors, even more preferably with an optical surface analyzer according to the phase shift channel of Candela CS20 and in particular with an optical surface analyzer according to FIG. 1.

31) Use of the gallium arsenide substrate according to one of the items 14-28 and 30 or respectively of the plurality of gallium arsenide substrates according to item 29 for epitaxial crystal growth, optionally after storage and preferably without pre-treatment after providing the gallium arsenide substrate and before the epitaxial crystal growth.

32) Use of the gallium arsenide substrate according to one of the items 14-28 and 30 or respectively of the plurality of gallium arsenide substrates according to item 29 for the production of semiconductor components or electronic and optoelectronic components.

33) Use of the gallium arsenide substrate according to one of the items 14-28 and 30 or respectively of the plurality of gallium arsenide substrates according to item 29 for the production of power components, high-frequency components, light-emitting diodes and lasers.

34) Use of an optical surface analyzer, particularly an optical surface analyzer analogous to Candela CS20 or specifically of the Candela CS20, for the optical contact-free quantitative characterization of the homogeneity of surface properties, particularly for the quantitative characterization of the homogeneity of the surface oxide layer, of gallium arsenide substrates by means of ellipsometric lateral substrate mapping.

35) The use according to item 34, wherein a laterally resolved measurement signal is corrected in regard to a background having lower frequency by means of discrete complex Fourier transformation, preferably using the Levenberg-Marquardt algorithm.

DETAILED DESCRIPTION OF THE INVENTION

Figure 1:
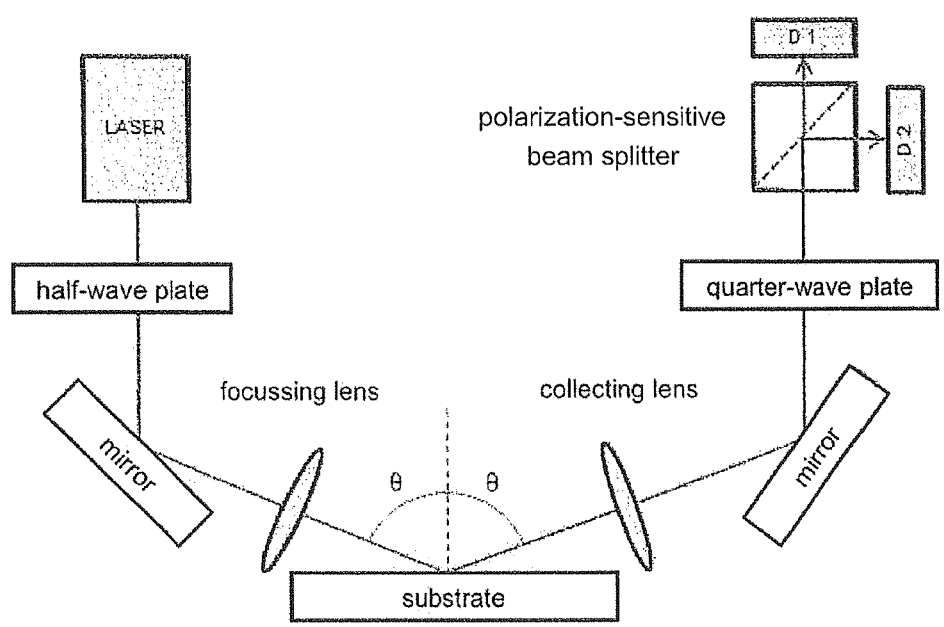
FIG. 1 schematically shows the optical setup and optical path of an optical surface analyzer according to Candela CS20 used for the ellipsometric surface measurements, in particular for the so-called phase shift channel of the measurement instrument Candela CS20.

Without limiting the present invention thereby, in the following the invention is illustrated by the detailed description of the Figures, aspects, embodiments and particular features, and particular embodiments are described in more detail.

A first aspect of the present invention provides a process for producing a surface-treated gallium arsenide substrate which comprises the following steps:

Providing a gallium arsenide substrate, oxidation treatment of at least one surface of the gallium arsenide substrate in dry condition by means of UV radiation and/or ozone gas, contacting of the at least one surface of the gallium arsenide substrate with at least one liquid medium and Marangoni drying of the gallium arsenide substrate.

In the process according to the invention it was surprisingly found that by the combination of the coordinately aligned dry oxidation treatment, the contacting with liquid medium and Marangoni drying the surface properties of the gallium arsenide substrate can be favorably and very homogeneously set, in particular the surface oxide. As a consequence, contrary to conventionally produced substrates, the surface oxide on the entire substrate surface can be thermally desorbed in a controlled and reproducible manner and practically from the entire substrate surface, for example immediately before the epitaxy in the epitaxy apparatus. In this way the substrate according to the invention can be used in the epitaxy process without further treatment. Here the gallium arsenide substrate can be a wafer.

In the present invention it was advantageously recognized that a very homogeneous surface is required since the thermal desorption behaviour and the thermal desorption temperatures of different oxides vary substantially and the thermal desorption behaviour of the oxide layer on a GaAs substrate depends on its composition of gallium and arsenic oxides of different oxidation states as well as the oxide layer thickness. Another advantage resides in that with the complete thermal desorption of the homogeneous oxide layer roughenings of the surface during the desorption of this oxide layer and thereby morphological perturbations in the epitaxially grown layer structures can be prevented. In the present invention it was further recognized that for a consistently high quality of the epitaxy layers over the entire wafer surface and hence for high yields the lateral surface homogeneity or respectively oxide homogeneity, that is the lateral uniformities of oxide composition and oxide thickness, are of great importance. In particular it was recognized that on parts of the GaAs surface having, compared to the rest of the wafer surface, a strongly differing, unfavorable oxide composition or oxide thickness a disturbed thermal desorption behaviour of the oxide can occur, whereby in turn remaining oxide islands or a stronger roughening of the wafer surface can result. The risk for the formation of crystallographic perturbations in the epitaxy layers can be very large at the disturbed regions, whereby the electrical functionality of the components produced from the GaAs wafer can be affected. It was furthermore advantageously recognized that for the setting of the surface properties the execution of the last steps within the production process of GaAs wafers, namely the final polishing and the subsequent cleaning steps, and thereof in particular the last cleaning steps immediately before the drying and the drying of the wafers, is of particular importance.

In consideration of the subsequent wet treatment and the specific drying step carried out thereafter it is of particular importance that for the production and cleaning process according to the present invention the surface of the GaAs substrate is homogeneously oxidized in dry condition before the contacting with liquid medium. The dry oxidation treatment according to the invention is carried out in one case by irradiation of the surface with UV light, preferably UV light of short wavelength. On the one hand the oxidation is initiated by the energy of the UV light itself. Furthermore, oxygen from the surroundings is partly converted by the light energy into ozone which enhances the oxidation process on the wafer surface. In another case the dry oxidation occurs through the exposure to ozone gas. The applied ozone gas can be produced by an ozone generator. Herein the dry oxidation effects the formation of a homogeneous passivating oxide layer as well as the oxidative destruction of organic impurities on the surface of the substrate. In the process a homogeneous surface oxide layer which in the subsequent steps serves as "sacrificial oxide" is formed in a controlled manner, laterally as well as depthwise. A deep oxidation of undefined surface states produced by the preceding process steps as well as the prevention of selectively acting oxide formation mechanisms which would occur in natural or wet chemical oxidation for the formation of a "sacrificial oxide" can be particularly advantageous. In the dry oxidation treatment the GaAs surface is oxidized more strongly towards bulk GaAs since the oxide on the front side grows partly in the direction of the wafer back side. Regions having surface properties differing from the rest of the wafer surface stemming from the preceding processes, which in the following are denoted as inhomogeneity defects, can subsequently be removed from the wafer surface more easily in the oxidized state, for example by wet chemical processes. A high quality of the oxide layer produced in the first step of the cleaning process is a prerequisite for the subsequent application of the contacting liquid medium, preferably a mildly erosive and roughness-neutral etching step. In the present invention it was furthermore particularly recognized that the dry oxidation is excellently suited to homogeneously hydrophylize the entire surface. This is particularly advantageous in view of a uniform wetting of the wafer surface during the transfer of the wafers between cleaning baths.

It was furthermore found that it is difficult to completely remove oxides from the GaAs surface which were created wet chemically. The homogeneity of the produced oxide layer and hence also (the degree and manner of) the removability of the produced oxide layer are significantly influenced by the oxidation conditions.

Subsequent to the dry oxidation treatment and the contacting of the surface with liquid medium, for example for suitable cleaning steps, according to the present invention the surface wetted with liquid medium is thereafter advantageously dried by Marangoni drying. Marangoni drying is based on the Marangoni principle. In the process a suitable agent is used, for example alcohol or other organic compounds, in particular isopropanol, which after its concentration at the surface of the liquid medium, for example at the water surface, reduces the surface tension of the liquid. When this liquid front, preferably the water front or respectively aqueous front, is moved relative to the surface of the wafer standing for example upright in the bath the gradient in the surface tension between the thin meniscus layer in contact with the wafer and regions of the liquid surface, preferably the water surface or respectively aqueous surface, further apart from the wafer causes a residue-free flowing-off of the liquid from the wafer surface.

Furthermore, the drying applied according to the invention is particularly advantageous for the cleaning of GaAs wafers with particularly small or particularly large thickness. In the Marangoni drying the wafers are subjected to less mechanical stress compared to spin drying which is generally used for the drying. In the present invention it was found that the risk and the tendency of wafer breakage for thin wafers during the cleaning of GaAs wafers according to the process of the present invention are considerably reduced. For thick GaAs wafers during the spin drying unbalance can occur at high revolution speeds due to the flats or notches applied for the marking of the crystallographic orientation, which likewise increases the risk of wafer breakage. Therefore, the present cleaning process also offers advantages for the cleaning of particularly thick GaAs wafers. In particular for the cleaning of large-area GaAs wafers, independent of the wafer thickness, still another advantage of the present invention follows: In the spin drying water residues are transported over the wafer surface up to the edge of the GaAs wafer which can lead to locally confined traces in the surface composition, so-called watermarks. In the Marangoni drying the drying always occurs immediately at the three-phase-boundary line between wafer, liquid level, preferably water level or respectively aqueous level, and the surrounding gas atmosphere. As a consequence, watermarks can be prevented for all substrate thicknesses and the GaAs substrate wafers can be dried homogeneously.

It has furthermore been surprisingly seen that in combination with the preceding dry oxidation treatment in the Marangoni drying in the present process an extremely homogeneous oxide layer is produced on the treated GaAs substrate surface with respect to thickness and composition. This is very advantageous for conventionally usual GaAs substrate thicknesses but in particular also for relatively thin or even extremely thin or respectively for relatively thick or even extremely thick GaAs substrates with simultaneously large diameter or respectively for large diameters and all substrate thicknesses. In this respect large diameters are at least 100 mm, preferably at least 150 mm and more preferably at least 200 mm. Substrate thicknesses can suitably be ≥100 µm; the maximum thickness can be determined by the desired application of a substrate, for example up to 5000 µm, usually preferably reaching up to 2000 µm or up to 1000 µm. In this way the cleaning sequence according to the invention enables the production of large-area GaAs wafers of various thickness having homogeneous surfaces.

The provided gallium arsenide substrate can be doped or undoped, is crystalline and particularly preferably monocrystalline, wherein the substrate can be produced by singularization or respectively separation from a GaAs bulk single-crystal body (ingot, boule). In an embodiment said provided gallium arsenide substrate was polished beforehand, preferably polished and subsequently pre-cleaned, more preferably polished and subsequently wet chemically pre-cleaned and particularly preferably polished and subsequently pre-cleaned wet chemically and with brush scrubbing. In this respect brush scrubbing can for example be advantageous to remove particles without the addition of organic surfactants. In the process according to the invention contaminations by particles and surface defects such as scratches, pits or bumps, crystal defects and severe roughnesses are prevented or greatly reduced. Owing to the achieved high homogeneity of the cover layer (the oxide layer), the produced GaAs wafer is particularly suited as substrate for the epitaxial growth of layers and layer systems, and, apart from the usual thermal desorption, can be immediately—optionally after intermediate storage—used for the epitaxy.

In a particular embodiment of the process according to the invention in step c) the following steps are comprised: The at least one surface of the gallium arsenide substrate is contacted with alkaline aqueous solution, optionally applying megasound, and subsequently with water. In particular possibly still present inhomogeneities in the oxide layer which lie very close to the surface of the wafer can advantageously and safely be removed.

In the process the wet cleaning with an alkaline cleaning step, optionally applying megasound, and with a water rinsing, preferably with deionized water (DI water) or ultrapure water is adjusted to the further process steps. During the transfer of the wafers between different baths of an automatically or manually operated wet process system a hydrophilic wafer surface is completely wetted with a liquid film.

In principle the prevention of dry regions on the wafer surface during the transport operations between the wet baths of a wet bench can also be achieved by carrying out the processes including the drying preferably in a single bath.

For this preferred embodiment of the process according to the invention a controlled removal of the oxide layer occurs by the alkaline cleaning appropriately in a first liquid bath. For the setting of the pH value in the simplest case ammonia, but also organic amine compounds can be added to the DI water. The concentration of the added chemicals can lie in the range of greater than 0.1 mass percentage (Ma %). The input of megasound in this bath supports the removal of particles adhering to the surface. In this regard megasound can be delivered to the bath either by applying appropriate transducers on a quartz glass tank from the outside or by applying appropriately coated vibrating elements directly in the bath.

In principle a removal of the oxide layer with simultaneous particle removal can alternatively also occur in an acidic cleaning medium.

When the oxide layer is removed in the alkaline medium, the high surface energy of the wafer surface is maintained by the increased presence of OH groups. The accordingly hydrophilic wetting behaviour of the surface stabilizes the surface homogeneity not only in the following transfer steps but also leads to a higher uniformity of the GaAs surface in the Marangoni drying.

According to a preferred embodiment subsequent to the alkaline cleaning preferably a rinsing of the wafers with DI water occurs. The process time of the rinsing can lie in the range from few seconds to several minutes depending on the respectively used concentration of the chemicals. The subsequent drying of the wafers according to the Marangoni principle is capable of effecting a very uniform drying of the wafer surface. Basic principle is the depression of the surface tension of the water or respectively the aqueous solution by the appropriate input of an appropriate agent such as for example isopropanol. The speed at which the wafers or respectively the water level or respectively aqueous level are moved can suitably be adjusted with respect to the surface energy of the wafers to be dried. In the process an optimum between quality and wafer throughput can be obtained. For GaAs substrate in the final stage of the wafer production appropriate drying speeds lie in the range of a few hundredths millimeters per second up to centimeters per second.

GaAs wafers dried according to the Marangoni process exhibit fewer traces of surface inhomogeneities compared to spin-dried wafers. This applies to both hydrophobic and hydrophilic spin-dried wafers.

The roughness of the GaAs surface is not changed by the removal of the oxide in the alkaline cleaning step and it remains at approximately 0.3 nm for $R_a$. Also the metallic surface contaminations determined by means of total reflection X-ray fluorescence (TXRF) analysis remain on the same level.

The cleaning sequence leads to an average particle contamination of at most 10 particles with a diameter in excess of 0.3 μm per substrate (KLA-Tencor Surfscan 6420). In this way with a cleaning sequence according to the preferred embodiment of the present invention the surface homogeneity is further improved. Roughness and metal contamination remain on the same level and the particle contamination is low.

GaAs wafers with a highly sensitive surface can be processed in the patch process with wet chemical cleaning using different types of wafer carriers. Since in the present invention preferably large-area GaAs wafers with a high surface homogeneity are produced, the use of wafer carriers which screen the wafer surface as little as possible is preferable. An even better possibility is to work completely without carrier. For the same reasons of an as homogeneous as possible wet treatment the flow conditions in the liquid baths are favorably set.

Figure 10:
FIGS. 10-12 show flow diagrams of different wet chemical cleaning treatments of GaAs wafers, in accordance with embodiments of the disclosure.

A preferred embodiment is exemplarily shown in the flowchart shown in FIG. 10.

Another embodiment of the process according to the invention is provided such that step c) further comprises the following steps: Subsequent to step ii) contacting of the at least one surface of the gallium arsenide substrate with acidic aqueous solution, optionally in the presence of an oxidizing agent, and subsequent further contacting of the at least one surface of the gallium arsenide substrate with water, wherein preferably the water at least initially contains a pH value modifying additive.

The etching medium here consists of an acid and optionally an oxidizing agent. Also this embodiment leads after the final drying of the wafer with the Marangoni process to a very uniform surface oxide.

Here hydrochloric acid or hydrofluoric acid can be used. $H_2O_2$ or ozone ($O_3$) dissolved in the liquid medium serve as oxidizing agent. In this further preferred embodiment all steps are coordinatively aligned such that i) inhomgeneities in the oxide layer and additionally also in the uppermost GaAs atom layers of the surface are removed, ii) by continuous complete wetting of the wafer surface during the transfer operations between the wet process steps no new inhomogeneity defects are produced, iii) by the specific configuration of the last rinsing step all oxide traces of the acidic cleaning step are uniformly removed and the GaAs surface is hydrophilized for the drying, and iv) by the Marangoni drying an extremely uniform wafer surface is obtained.

The acidic cleaning serves inter alia to remove metallic contaminations. By the selection of the concentrations of acid and oxidizing agent, considering the high reactivity of the GaAs surface, the strength of the reaction and thus the etching abrasion as well as the roughening of the surface can be controlled. On the basis of the high reactivity of the GaAs surface the conditions are advantageously selected such that substantially no, preferably no, locally different oxide thicknesses, oxide compositions or roughenings, also inhomogeneity defects, form on the surface of the GaAs wafers.

In the present invention suitable conditions and compositions for the oxidizing acidic cleaning step can be selected for which such a preferable abrasion of possible inhomogeneity defects from the preceding processes is possible on GaAs wafers, wherein in this cleaning step the roughness after the last polishing step is at least preserved.

Typical oxidizing agents for the cleaning of semiconductor wafers in aqueous solutions are hydrogen peroxide and ozone. As oxide dissolving acids preferably hydrofluoric acid or hydrochloric acid are used.

According to this preferred embodiment of the present invention in comprehensive investigations conditions were found for which a removal of possible inhomogeneity defects is possible, the re-contamination by particles remains low and the roughness obtained in the last polishing step remains constant. For this purpose the acid concentration preferably is less than 0.25% and greater than 0.1%, determined as percent by volume in the whole liquid. The rate of the material abrasion can be determined substantially by the concentration of the oxidizing agent. This way a typical $R_a$ roughness of 0.30±0.03 nm after the last polishing step can be improved up to 0.20±0.03 nm in the entire ozone concentration range.

The etching abrasion to be preferably carried out according to this embodiment occurs on the basis of simultaneous oxide formation and oxide removing processes. When the wafers are extracted from the acidic etching liquid for the transfer to the following liquid bath, they are covered on their surface with an oxide layer. Due to the simultaneously hydrophobizing effect of the acid in this case the wafers are not automatically completely wetted during the transfer despite the oxide layer. Rather also the wetting behaviour after the acidic cleaning step here is advantageously determined by the balance between acid and oxidizing agent. A good wetting behaviour of the GaAs wafers is required also during this transfer operation in order to prevent for the reasons mentioned above local perturbations of the oxide homogeneity in the dry regions. In the investigations carried out it was seen that also for the reason of good wettability the acid concentration is preferably kept below 0.25%.

Using more than 20 ppm ozone and HCl in low concentrations below 0.5% as well as applying appropriate transfer times, during the transfer the GaAs wafers in air remain completely wetted. From this follows the particularly preferable configuration for the acidic cleaning step in this embodiment of the present invention. Particularly favorable is the use of HCl with a concentration between 0.15 and 0.25% together with ozone in a concentration of 10-100 ppm and a dwell time of the wafers in this solution between 2 minutes and 5 minutes.

More preferably, after the acidic cleaning in the presence of an oxidizing agent, the subsequent cleaning step is carried out with addition of a pH value modifying substance ("spiking"). Such an additional step can be suitably adjusted with respect to the preceding acidic cleaning step as well as the subsequent Marangoni drying, and it can contribute to prevent a possible regeneration of inhomogeneities. By adding an acidically or basically acting substance to the circulation loop of the rinsing bath, the oxide layer on the GaAs wafer is immediately removed uniformly during the immersion of the wafer. Possible inhomogeneity defects are prevented using ammonia but also when applying HCl. After the pH modified rinsing water circulates around the wafers for a short time, preferably fresh water is delivered and the actual rinsing of the wafers with fresh DI water starts. For the removal of the oxide layer in the rinsing step acidically as well as basically acting chemicals are suitable. The roughness of the GaAs surface is not increased during the gently abrasive etching in the preferred concentration region of the pH modifying substance with respect to the roughness before the cleaning sequence and it remains at least at typically 0.3±0.03 nm for $R_a$.

According to the invention it can be achieved that the metallic surface contaminations determined by means of TXRF remain on the same low level. The average particle contamination with this cleaning sequence is around 10 particles having a diameter in excess of 0.3 µm per wafer (KLA-Tencor Surfscan 6420). This way with a cleaning sequence according to this preferred embodiment of the present invention the surface homogeneity is improved. Roughness and metal contamination remain at least on the same level and the particle contamination is low.

Figure 11:
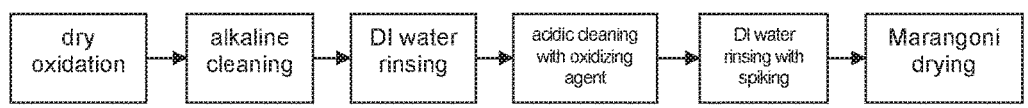

This particularly preferable embodiment is exemplarily shown in the flowchart shown in FIG. 11.

In a further embodiment of the process according to the invention in step c) subsequent to step iv) further steps according to steps i) and ii) are carried out. In this embodiment after acidic cleaning and subsequent rinsing the wafers are subjected before the drying yet a further alkaline cleaning, optionally and preferably with exposure to megasound. This way a still more effective particle removal is possible compared to the application of megasound in the DI water rinsing bath. Furthermore, the hydrophilic character of the GaAs surface is increased by the alkaline treatment which has a favorable effect on the behaviour of the wafers during drying.

Figure 12:
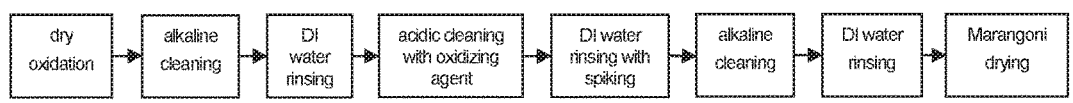

The embodiment is exemplarily shown in the flowchart shown in FIG. 12.

Another aspect of the present invention is a process for producing a plurality of surface-treated gallium arsenide substrates, wherein simultaneously a plurality of gallium arsenide substrates in the process according to one of the preceding items is subjected to the respective steps b)-d).

The batch-wise production of a plurality of wafers enables on the one hand an economic production, but on the other hand also a high homogeneity of the product properties, in particular the surface properties, of the substrates among one another.

A further aspect of the present invention is a gallium arsenide substrate which exhibits at least one surface having in ellipsometric lateral substrate mapping with an optical surface analyzer a variation of the laterally resolved background-corrected measurement signal whose distribution percentile of 1% normalized to the substrate average of the phase shift signal, i.e. for the distribution the 1% percentile, is greater than −0.0065, preferably greater than −0.0060, more preferably greater than −0.0055, even more preferably greater than −0.0050, still more preferably greater than −0.0045, particularly preferably greater than −0.0040, in particular greater than −0.0030, especially greater than −0.0020, preferably greater than −0.0010 and even up to 0.0000, wherein the absolute value 0.0000 can be excluded.

Phase shift signal denotes a measured or respectively detected signal which is based on phase-dependent properties of differently polarized light components, for example of perpendicularly and parallel polarized light. Preferably the phase shift signal is measured as intensity difference between detector signals, more preferably two detectors detect differently polarized light components of laser light reflected from the substrate surface, wherein the differently polarized light components after interaction of laser light and substrate are additionally spatially separated.

The substrate average of the phase shift signal is the arithmetic mean of all phase shift signals measured on a substrate.

All deviations from the ideal homogeneous surface (residuals of the background-corrected mapping of the phase shift signals) can be presented in a histogram. Since this distribution typically does not correspond to a Gaussian normal distribution, the frequently used standard deviation cannot be used as a measure of homogeneity. Rather it is expedient to define and to compute appropriate percentiles. For the evaluation of the homogeneity of the GaAs surfaces according to the present invention, the percentiles P1 or respectively $Q_{0.01}$ are used for comparisons. Distribution percentile of 1% or respectively 1% percentile for the distribution denotes the percentile rank P1 below which lie 1% of the total number of values of the distribution, and it correspond to the quantile $Q_{0.01}$ (see for example F. Schoonjans, D. De Bacquer, P. Schmid P, "Estimation of population percentiles". Epidemiology, 22, 2011, p. 750-751). In order to compensate for fluctuations of the irradiated light intensity the determined percentiles are normalized to the respective wafer averages of the phase shift signal, i.e. they are divided by the arithmetic mean of all phase shift signals measured on a substrate.

Another aspect of the present invention is a gallium arsenide substrate which exhibits at least one surface having in background-corrected ellipsometric lateral substrate mapping with an optical surface analyzer, with respect to a substrate diameter of 150 mm as reference, a defect number of <6000, preferably <5000, more preferably <4000, even more preferably <3000, still more preferably <2000, yet more preferably <1000, still more preferably <500, still more preferably <300, still more preferably <250, still more preferably <200, still more preferably <150 and particularly preferably <100 and/or a total defect area of less than 2 $cm^2$, preferably less than 1 $cm^2$, more preferably less than 0.5 $cm^2$, even more preferably less than 0.1 $cm^2$, still more preferably less than 0.05 $cm^2$, still more preferably less than 0.01 $cm^2$, still more preferably less than 0.005 $cm^2$ and particularly preferably less than 0.0035 $cm^2$, wherein a defect is defined as a continuous area greater than 1000 $\mu m^2$ having a deviation from the average measurement signal in ellipsometric lateral substrate mapping with an optical surface analyzer of at least ±0.05%. With the designated measurement values an adequate differentiation of the gallium arsenide substrates according to the invention, determinable analytically by means of the described ellipsometric lateral substrate mapping, versus conventional gallium arsenide substrates is given (see e.g. also the Examples described below).

The ellipsometric lateral substrate mapping is preferably carried out with an optical surface analyzer analogous to Candela CS20, more preferably specifically with the optical surface analyzer Candela CS20. In particular optical surface analyzers are suitable for which the used analysis laser light uses a wavelength of 405 nm and whose optical path comprises a half-wave plate, a quarter-wave plate, a polarization-sensitive beam splitter and two detectors. Specifically an optical surface analyzer can for example operate according to the phase shift channel of Candela CS20; a typically usable configuration for a preferable optical surface analyzer is shown in FIG. 1.

Ellipsometry is based on the interaction of polarized light during its propagation in optically active media. The selection of an appropriate light wavelength as well as the measurement configuration in reflection enable a high surface sensitivity. FIG. 1 schematically shows the optical setup and optical path of an optical surface analyzer according to Candela CS20 used for the ellipsometric surface measurements, i.e. for ellipsometric lateral substrate mappings, of the present invention, in particular for the so-called "phase shift" channel of the measurement apparatus Candela CS20 from the company KLA-Tencor. Here for the characterization of GaAs substrate surfaces the polarized light of a laser having a wavelength of 405 nm is used which after passing through a half-wave plate is directed by a mirror and a focussing lens onto the substrate surface at an angle (θ) of 60° with respect to the normal. The perpendicular and parallel polarized components are reflected at the substrate surface according to the optical properties of the oxide layer and are sent through a collecting lens, via a mirror and a quarter wave-plate onto a polarization-sensitive beam splitter. Here the differently polarized light components resulting from the interaction with the substrate surface are separated and analyzed in the detectors D1 and D2. According to a preferred embodiment the intensity difference between the detector signals is denoted as phase shift signal, and the phase shift signal ("phase shift") characterizes the optical properties of the reflecting substrate surface. By means of rotation of the wafer and simultaneous radial movement of the optical measurement system the complete surface of the wafer can be scanned in a spiral pattern. By fast ellipsometric mapping or respectively scanning complete highly resolved mappings or respectively images of the optical properties can also be generated for large-area GaAs substrates (substrate mappings) for the assessment of the surface homogeneity. According to the invention an optical surface analyzer analogous to Candela CS20 from the company KLA-Tencor can be used, i.e. a measurement device corresponding to a Candela CS20, in particular however the apparatus Candela CS20 is preferably used (see also L. Bechtler, V. Velidandla, Proc. SPIE 4944, Integrated Optical Devices: Fabrication and Testing, 109, 2003; doi:10.1117/12.468295 and F. Burkeen, Compound Semiconductor, 14 (10), 2008), in particular the phase shift channel of Candela CS20. In principle however similar or different ellipsometric measurement devices and mapping ellipsometers can be applied, wherein depending on the respective optical setups, optical paths and measurement principles a corresponding adaptation can occur.

Figure 2:
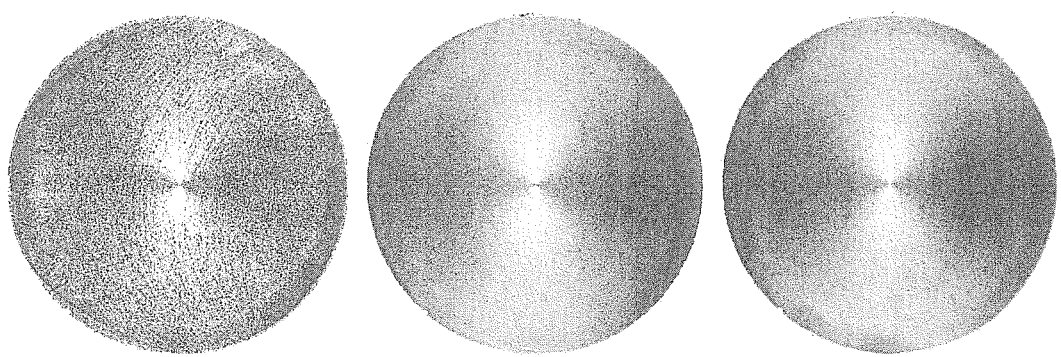
FIG. 2 shows typical ellipsometric lateral substrate maps, so-called Candela images, for different final cleaning technologies (from left to right: Comparative Example 1, Example 1 and Example 2).

For the measurement the Candela CS20 uses the interaction of a laser beam having a wavelength of 405 nm which impinges on the wafer surface at an angle of 60° relative to the normal. By rotation of the wafer and simultaneous radial movement of the optical measurement system the complete surface of the wafer can be scanned in a spiral pattern. The single intensity measured at each point is depicted by color coding or also by coding with levels of grey or pseudo-colors in a highly resolved image (substrate mapping). FIG. 2 shows typical ellipsometric lateral substrate maps, so-called Candela images, for different final cleaning technologies. The anisotropic reflection properties of GaAs as well as variations of the optical properties of the transparent surface oxide layer, which can for example be caused by contaminations or a non-uniform wet cleaning of the wafers, lead to a locally differing reflection behaviour as a result of changed layer thicknesses and/or indices of refraction. Thereby local fluctuations of the phase shift occur which can be quantitatively investigated as a measure for the surface homogeneity or respectively for the optical homogeneity of the oxide layer.

The radial and azimuthal resolutions can be set in a very large range. For the characterization of large-area GaAs wafers the selection of a radial resolution of 50 μm (or respectively 45 μm at 5 μm beam width) and an azimuthal resolution of 16384 measurement points per trace/track (corresponding to a resolution of 29 μm or respectively 25 μm after subtraction of the beam diameter in the outer circumference of a 150 mm wafer or respectively 0.01 μm in the inner-most measurement circle) has been found to be appropriate.

The Candela measurement system combines four different detectors for the simultaneous measurement of the scattering intensity, the topography, the reflectivity and the phase shift of the gallium arsenide substrate. This combination enables a comprehensive characterization and defect detection with respect to contaminations by process residues, point defects, topographical anomalies and surface or respectively (oxide) layer homogeneity of the gallium arsenide substrate. For the characterization of the homogeneity of the surface according to the present invention the phase shift ("phase shift" channel) is used. The measurement principle is explained in more detail, referring again to the schematic illustration of FIG. 1. For this particular form of an ellipsometric measurement the laser beam impinging on the wafer surface is polarized in a specific manner. Denoted as Q-polarization, it is a mixed form of perpendicularly and parallel impinging beam components which are respectively linearly polarized. Without being bound to this theory, it is assumed that different reflection behaviour of both components at the surface of the oxide layer and at the interface between oxide layer and substrate as well as different refraction behaviour within the oxide layer causes an optical path length difference between s component and p component in the reflected laser beam leading as a consequence to a phase shift between both components. This phase shift can be determined after the optical splitting of both components and their spatially separated detection as difference of the signals of both detectors. Without being bound to this theory, it is further assumed that changes of the optical properties of the transparent surface oxide layer, which can for example be caused by contaminations or a non-uniform wet cleaning of the wafers, lead to a locally differing light refraction and reflection behaviour as a result of changed layer thicknesses and/or indices of refraction. Thereby local fluctuations of the phase shift occur which can be quantitatively investigated as a measure for the surface homogeneity or respectively for the optical homogeneity of the oxide layer. In the mapping generated in the measurement local differences of these layer properties are depicted as differences in intensity. The high resolution of the measurement method and the high sensitivity lead to a very exact depiction of the optical surface properties, which is not or at least not usually obtainable other than with the ellipsometers described and defined here.

Figure 3:
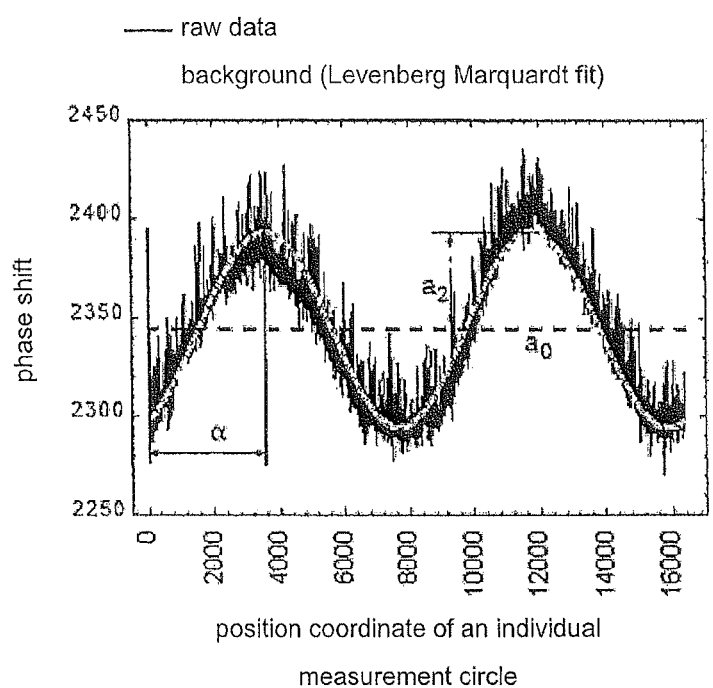
FIG. 3 exemplarily illustrates the measured signal curve ("raw data") of a circular track, wherein the curve "background" describes the crystallographically caused part of the measurement signal, wherein this part can be modeled by Fourier transformation using the Levenberg-Marquardt algorithm.

In the measurement of GaAs surfaces a crystallographically caused, two-fold anisotropic reflection of the light occurs. The signal variation associated therewith is superimposed on the actual measurement signal. In order to improve the sensitivity of the method, the two-fold intensity variations of the background caused by the anisotropic reflection are corrected. For the data tracks recorded for example in a spiral or circular form the two-fold profile is modeled by means of discrete complex Fourier transformation with appropriate frequencies using the Levenberg-Marquardt algorithm (see for example J. J. Moré, in G. A. Watson (ed.): Numerical Analysis. Dundee 1977, Lecture Notes Math. 630, 1978, p. 105-116) according to the following equation:

$$f(\varphi)=a_0+a_2\cos(4\pi\varphi+\alpha),$$

wherein φ is the function variable, α is an angle offset, $a_0$ is the absolute offset and $a_2$ is the amplitude of the model function. FIG. 3 presents exemplarily a typical, measured signal curve (raw data) of a circular track (trace), i.e. along a measurement circle as a function of the position coordinate, wherein the line "background" describes the crystallographically caused part of the measurement signal which can be modeled by Fourier transformation using the Levenberg-Marquardt algorithm. Here, the long-wave, crystallographically caused background oscillation can be separated from the part of the measurement signal stemming from the surface properties by modeling the two-fold profile for each circularly recorded data track by means of discrete complex Fourier transformation with appropriate frequencies using the Levenberg-Marquardt algorithm using the cosine function given above.

Figure 4:
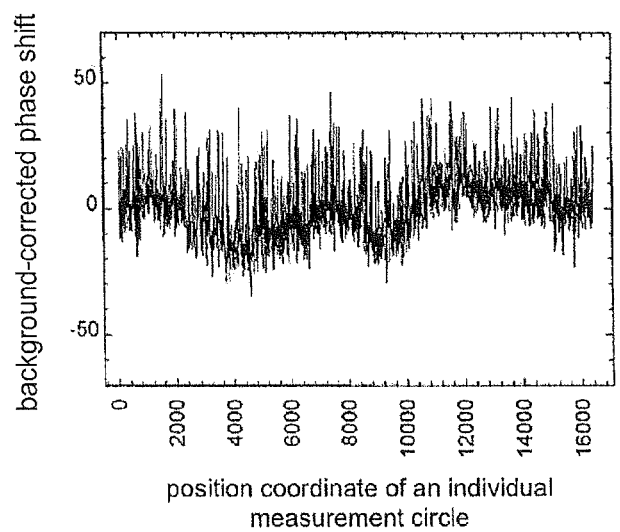
FIG. 4 exemplarily shows determined phase shifts of a track after subtraction of the crystallographically caused background signal.

FIG. 4 exemplarily shows determined phase shifts of a track after subtraction of the crystallographically caused background signal, i.e. a typical curve of the measurement signal along a measurement circle as a function of the position coordinate after the subtraction of the crystallographically caused background oscillation is shown. This corresponds to the laterally resolved background-corrected measurement signal.

Figure 5:
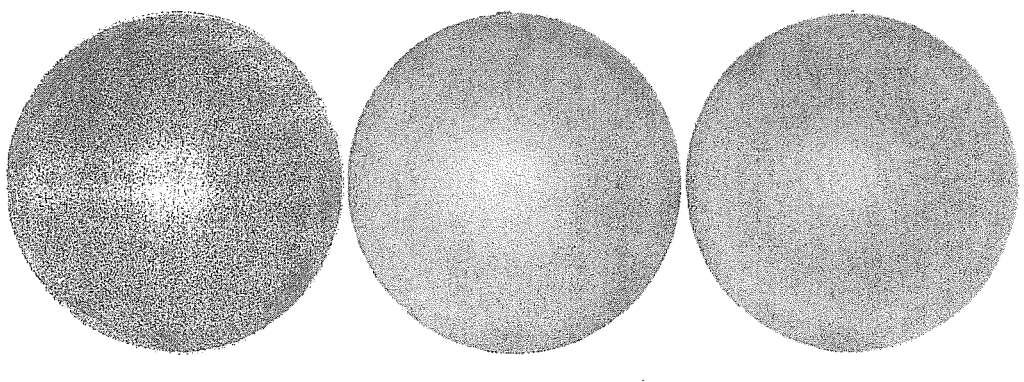
FIG. 5 shows typical ellipsometric lateral substrate maps, so-called Candela images, after subtraction of the crystallographically caused background signal for different final cleaning technologies (from left to right: Comparative Example 1, Example 1 and Example 2).

The background-corrected mappings now no longer show a two-fold symmetry which could interfere with the characterization of deviations of the homogeneity of the surface properties. This is on the one hand illustrated in FIG. 5 for typical ellipsometric lateral substrate maps, so-called Candela images, after subtraction or respectively correction of the crystallographically caused background signal for different final cleaning technologies. Inhomogeneities of the surface properties now emerge more strongly (cf. FIG. 2).

Figure 6:
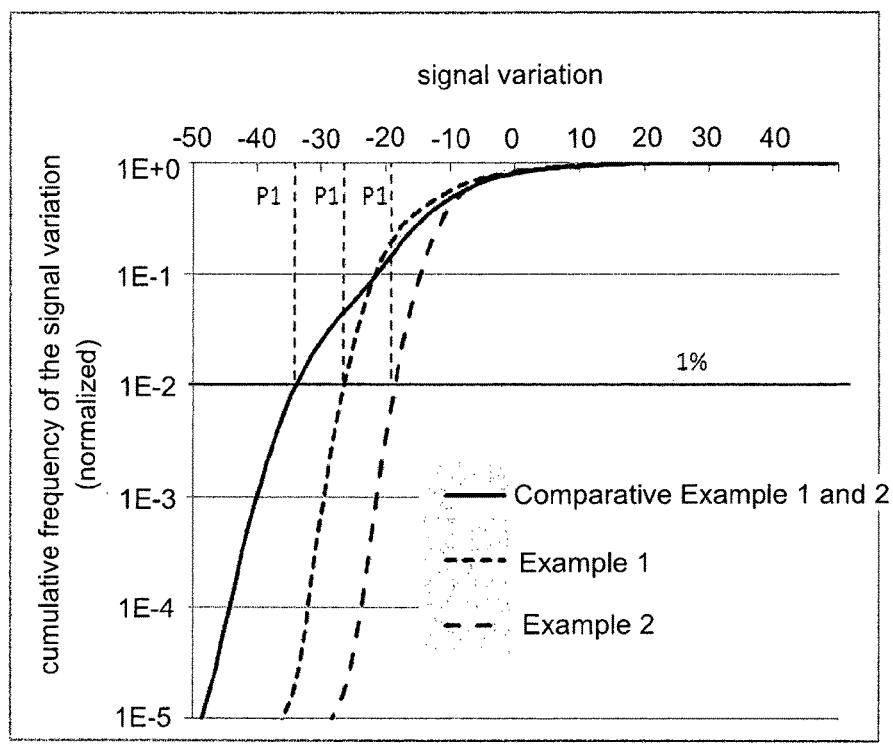
FIG. 6 presents typical global frequency distributions of the background-corrected phase shifts, i.e. residuals of the background-corrected mappings, for respectively individual wafers subjected to respectively different final cleaning technologies.
Figure 6:
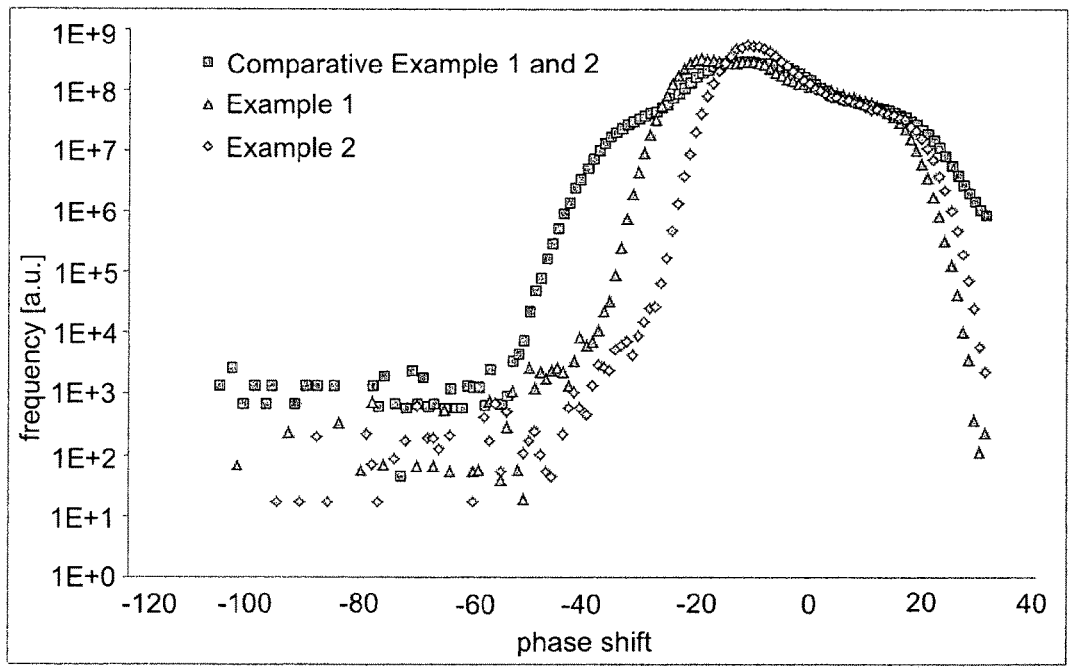

Furthermore, all deviations from the ideal homogeneous surface (residuals of the background-corrected mappings) can be represented in a histogram. FIG. 6 depicts typical global frequency distributions of the background-corrected phase shifts, i.e. residuals of the background-corrected mappings, for different final cleaning technologies. Since this distribution typically does not correspond to a Gaussian normal distribution, the frequently used standard deviation cannot be used as a measure of homogeneity. Rather, it is expedient to define and to compute appropriate percentiles. For the evaluation of the homogeneity of the GaAs surfaces according to the present invention the percentiles P1 or respectively $Q_{0.01}$ (see for example F. Schoonjans, D. De Bacquer, P. Schmid P, "Estimation of population percentiles". Epidemiology, 22, 2011, p. 750-751) were used for comparisons.

Figure 7:
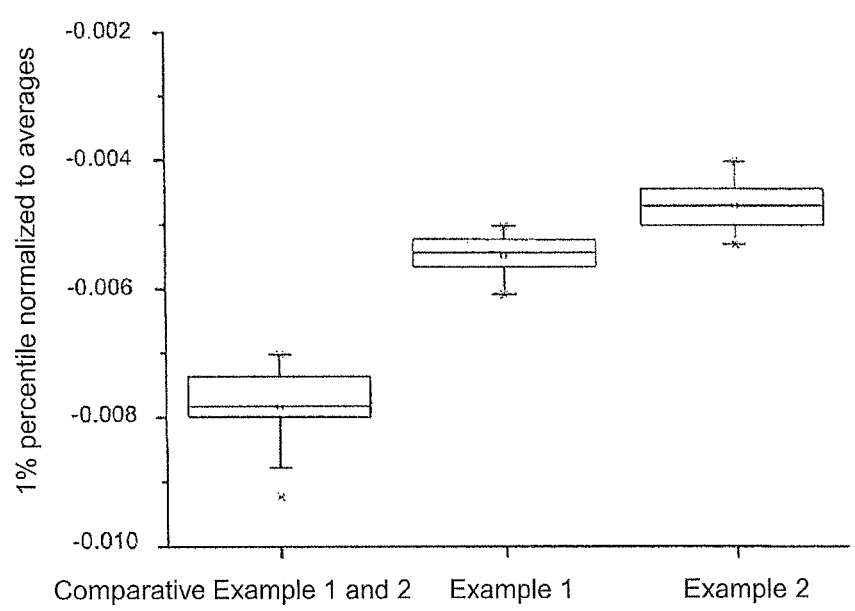
FIG. 7 shows typical 1% percentiles of in each case 25 wafers produced according to the methods from the Comparative Examples 1 and 2 or respectively the Examples 1 and 2 according to the invention. For an objective comparison of the percentiles said 1% percentiles are normalized to the respective wafer averages of the phase shift signals.

FIG. 7 presents in a comparison typical 1% percentiles of an appropriate plurality of substrates/wafers—here specifically of respectively 25 wafers—, which were produced according to the methods of Comparative Example 1 and 2 as well as Example 1 and 2 described below, wherein the percentiles are normalized to the respective wafer averages of the phase shift signal in order to compensate for fluctuations of the irradiated light intensity. For the statistical representation so-called box-and-whisker plots are used (see for example P. J. Govaerts, T. Somers, F. E. Offeciers, Otolaryngology—Head and Neck Surgery, 118(6), June 1998, p. 892-895 and J. W. Tukey: Exploratory data analysis. Addison-Wesley 1977, ISBN 0-201-07616-0). On the basis of the respective 1% percentiles of the single deviations of the phase shift of the light reflection normalized to the wafer average of the phase shift signals, which can be used for the assessment of the homogeneity of the GaAs surfaces, from FIG. 7 (see also Examples 1-2 and Comparative Examples 1 and 2) it can be seen that the so far usual technology produces wafers with surface homogeneities which exhibit 1% percentiles, as defined above, of less than −0.0065. The differences between the wafers according to the invention and the comparative wafers are significant and reproducible. Generally and as demonstrated here in detail, the wafers according to the invention, contrary to comparative wafers, show values of greater than −0.0065, preferably greater than −0.0060, more preferably greater than −0.0055, even more preferably greater than −0.0050, still more preferably greater than −0.0045 and particularly preferably greater than −0.0040. Even values of greater than −0.0030, preferably greater than −0.0020, more preferably greater than −0.0010 and up to 0.0000 excluding 0.0000 come into consideration.

Alternatively the background-corrected mappings can also be characterized by means of defect classification, for example with the analysis software made available and correspondingly described according to Candela CS20. The mappings show light and dark regions as well as stripe structures which can be assigned to inhomogeneities or respectively generally "defects". The intensity and the number of the deviations from the background characterize the homogeneity of a surface. The intensity differences are classified and counted with respect to their strength and areal extension. Particular parameters are selected with which the signals to be analyzed and the defects to be analyzed are defined. In the present case with the analysis software of the Candela CS20 in particular the following definitions were made (cf. Table 1 for the present definition of the measurement signals to be analyzed).

TABLE 1

| Signal type | Neg. deviation [%] | Pos. deviation [%] | Kernel length [μm] | Kernel type | Radial stitching [pixel] | Circular stitching [pixel] |
| --- | --- | --- | --- | --- | --- | --- |
| QAbsPhase | 0.05 | 0.05 | 1000 | median | 10 | 10 |

Figure 8:
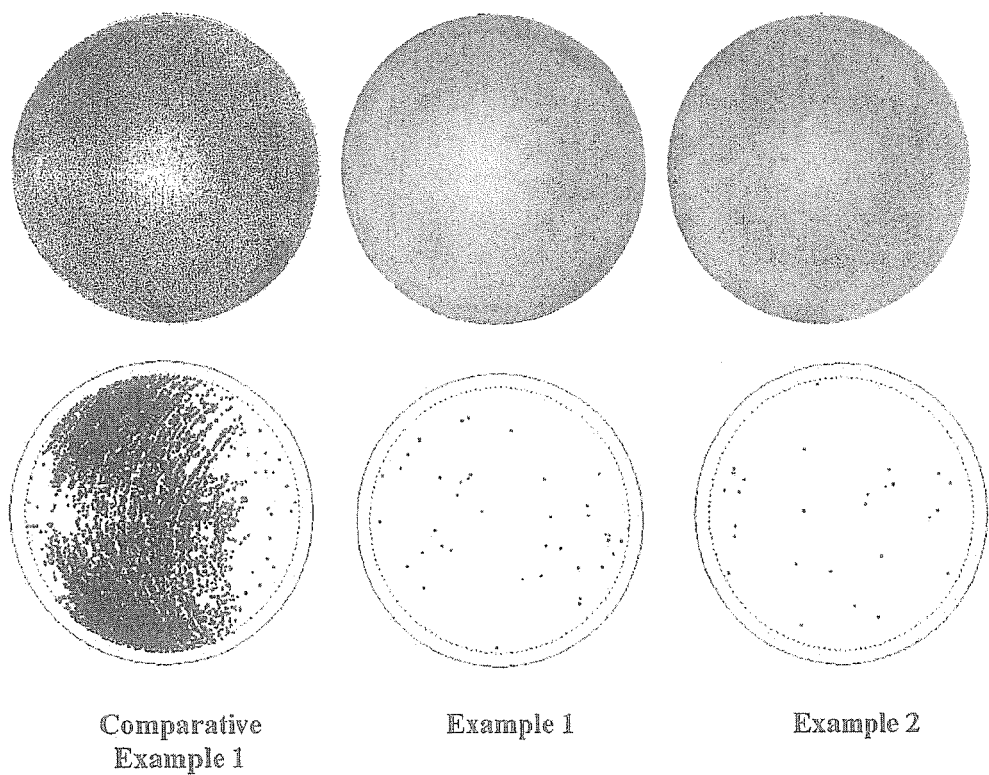
FIG. 8 shows typical so-called defect maps of background-corrected Candela images for different final cleaning technologies (from left to right: Comparative Example 1, Example 1 and Example 2).

The negative and positive intensity oscillations (deviations) are taken into account from a threshold value of 0.05%. The kernel length describes the averaging area, the kernel type denotes the kind of averaging. In case the positive and negative exceedances of the threshold values fulfill the distance criteria defined under "radial stitching" and "circular stitching" they are counted as individual defects and summed-up over the wafer. In this respect the stitching parameters specify the minimum distance of measurements points which positive or negative exceedances must exhibit in order to be counted as separate defects. Defects whose detected area is greater than 1000 μm$^2$ have been found to be relevant. The sum of defects counted in such a manner is a measure for the homogeneity of a wafer. FIG. 8 shows typical so-called defect maps of background-corrected Candela images for different final cleaning technologies. Such defect maps can serve the defect classification. For this purpose the analysis software of the measurement apparatus Candela CS20 is used as described above in which the intensity differences of the phase shift are classified and counted with respect to their strength and areal extension. The sum of such defects is a measure for the homogeneity of a substrate or respectively wafer. For substrates or respectively wafers produced according to so far usual technology, based on substrate or respectively wafer diameters of 150 mm as reference, defect numbers of >6000 and/or defect areas of >2 cm$^2$ are obtained. Substrates or respectively wafers of the invention which can be produced by the process according to the invention show, based on substrate or respectively wafer diameters of 150 mm as reference, defect numbers of <6000, preferably <5000, more preferably <4000, even more preferably <3000, still more preferably <2000, still more preferably <1000, still more preferably <500, still more preferably <300, still more preferably <250, still more preferably <200, still more preferably <150 and particularly preferably <100, and/or they show defect areas of <2 cm$^2$, preferably <1 cm$^2$, more preferably <0.5 cm$^2$, even more preferably <0.1 cm$^2$, still more preferably <0.05 cm$^2$, still more preferably <0.01 cm$^2$, still more preferably <0.005 cm$^2$ and particularly preferably <0.0035 cm$^2$.

Figure 9:
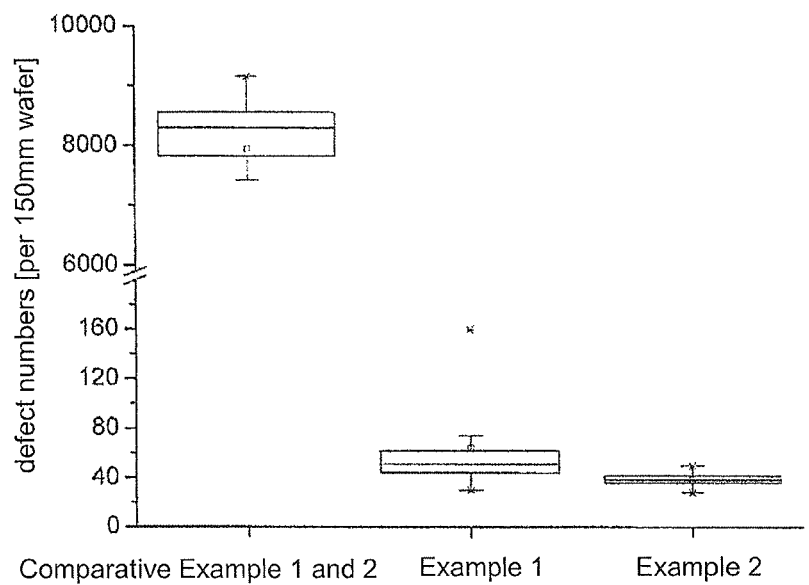
FIG. 9 shows typical defect numbers and defect areas of in each case 25 wafers produced according to the methods from the Comparative Examples 1 and 2 or respectively the Examples 1 and 2 according to the invention.
Figure 9:
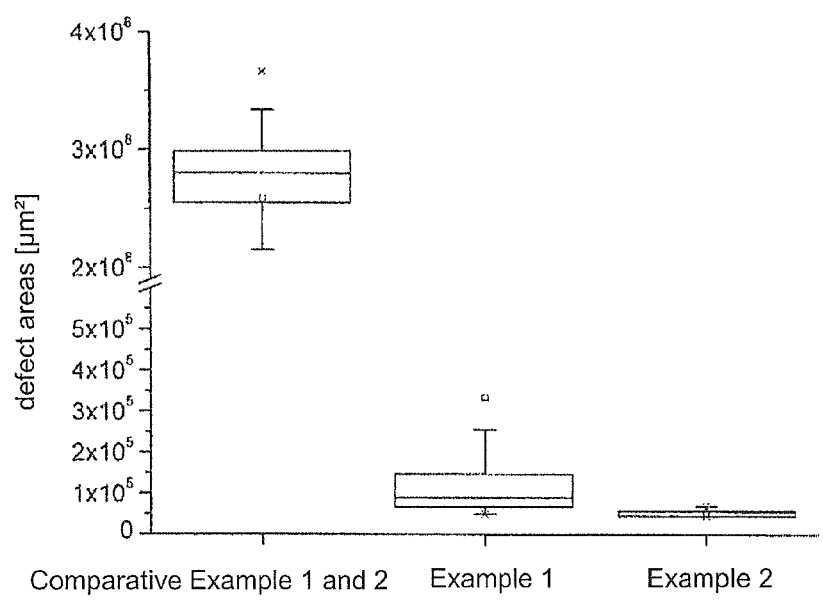

For a comparison of conventional values and values according to the invention for defect number and defect area see also FIG. 9 as well as Examples 1 and 2 and Comparative Examples 1 and 2. FIG. 9 shows typical defect numbers and defect areas of respectively 25 wafers which were produced according to conventional processes (cf. Comparative Examples 1 and 2) and according to processes of the invention (cf. Examples 1-2). The differences between the wafers according to the invention and the comparative wafers are significant and reproducible.

In a further aspect said gallium arsenide substrate can exhibit a diameter of at least 100 mm, preferably at least 150 mm and more preferably at least 200 mm.

The obtainable advantageous features and properties of the GaAs wafers obtained according to the invention are usable not only for the conventionally used thickness of GaAs wafers, that is approximately in the range of ca. 600 μm to ca. 800 μm and specifically with the conventional standard thickness of ca. 675 μm (±25 μm). Rather now also significantly thinner and thicker GaAs wafers are accessible. Particularly the altogether more gentle treatment and the very homogeneous and significantly defect-reduced surface properties according to the present invention contribute to this.

In an independent aspect the present invention thus provides for the first time finished gallium arsenide substrates with thickness ranges which because of the so far not obtainable product properties were not taken in consideration, namely exhibiting a thickness in the range of ≥approximately 600 μm and alternatively a thickness in the range of approximately 800 μm. More preferable thickness ranges lie for the thinner substrates in a range of approximately 100 up to approximately 600 μm, more preferably in a range of approximately 250 to approximately 500 μm, or respectively for the thicker substrates in a range of approximately 800 to approximately 2000 μm. The diameter of the gallium arsenide substrates according to the invention preferably is at least 150 mm. The gallium arsenide substrate products provided according to the invention are finished (finally processed), i.e. at least surface-finished and preferably polished and surface-finished. The surface final treatment comprises in particular an oxidation treatment of at least one surface of the gallium arsenide substrate in dry condition by means of UV radiation and/or ozone gas, a contacting of the at least one surface of the gallium arsenide substrate with at least one liquid medium and a Marangoni drying of the gallium arsenide substrate. For the polishing of the GaAs surface commonly known procedures can be carried out. Here for the surface final treatment it is referred to the further description of the process according to the invention.

The treated surface of the polished and surface-finished gallium arsenide substrate exhibits preferably the surface features already described above in connection with the ellipsometric lateral substrate mapping with an optical surface analyzer to which reference is made hereby. Finished gallium arsenide substrates processed according to the invention can therefore alternatively be characterized as follows: (i) by the in comparison to the standard thickness relatively thinner or relatively thicker layer thickness; (ii) by the properties which contrary to the conventional final treatments are obtainable only by the surface final treatment according to the invention; and (iii) by the differences determinable by means of ellipsometric lateral substrate mapping with an optical surface analyzer. It is referred to further explanations and definitions given in this application.

The term "approximately" or respectively "ca." used herein signifies that practically a specification of an exact value does not necessarily matter, rather tolerances of for example ±25 μm are possible, wherein preferable tolerance ranges are ±20 μm, more preferably ±15 μm, even more preferably ±10 μm, and particularly preferably ±5 μm.

The gallium arsenide substrate according to the invention can be doped or undoped.

Another aspect of the present invention provides a gallium arsenide substrate which exhibits at least one surface having within 9 months, preferably 12 months, after the production a substantially not deteriorating, preferably a not deteriorating, variation of the laterally resolved background-corrected measurement signal in ellipsometric lateral substrate mapping with an optical surface analyzer.

"Substantially" here denotes a change of ≤10%, preferably ≤5%, of the distribution percentile of 1% normalized to the substrate average of the phase shift signal and/or, based on a substrate diameter of 150 mm as reference, of the defect number and/or the total defect area, wherein reference is made to the preceding explanations and definitions of distribution percentile of 1%, defect number and total defect area.

A further aspect of the present invention provides a gallium arsenide substrate, wherein the at least one surface within 6 months after the production exhibits a substantially not deteriorating, preferably a not deteriorating, variation of the laterally resolved background-corrected measurement signal in ellipsometric lateral substrate mapping with an optical surface analyzer.

"Substantially" here denotes a change of ≤10%, preferably ≤5%, of the distribution percentile of 1% normalized to the substrate average of the phase shift signal and/or, based on a substrate diameter of 150 mm as reference, of the defect number and/or the total defect area, wherein reference is made to the preceding explanations and definitions of distribution percentile of 1%, defect number and total defect area.

By the process according to the invention not only a very homogeneous surface is set in a large area, but it is also advantageously maintained in a very stable manner over a period of time of at least 6 months, preferably 9 months, more preferably 12 months. This is tested and confirmed by Candela measurements in the course of time after production. In this regard an appropriate storage, in particular a storage of the substrate in darkness under particle-free inert gas atmosphere (e.g. N$_2$), can contribute to the longer stability of the substrate surface.

Another aspect according to the invention is a plurality of gallium arsenide substrates which are produced according to the process of the invention and which among one another exhibit a substantially same, preferably same, variation from substrate to substrate of the laterally resolved background-corrected measurement signal in ellipsometric lateral substrate mapping of the respective at least one surface with an optical surface analyzer.

"Substantially" here denotes a change of ≤10%, preferably ≤5%, of the distribution percentile of 1% normalized to the substrate average of the phase shift signal and/or, based on a substrate diameter of 150 mm as reference, of the defect number and/or the total defect area, wherein reference is made to the preceding explanations and definitions of distribution percentile of 1%, defect number and total defect area.

As a result of the very reproducible process and the possibility of batch-wise production a plurality of GaAs substrates is obtained which among one another exhibit only a very small variability as regards their surface properties. This is tested and confirmed by means of ellipsometric Candela mapping.

A further aspect according to the invention is the use of the gallium arsenide substrate according to the present invention for epitaxial crystal growth, optionally after storage and preferably without pre-treatment after providing the gallium arsenide substrate and before the epitaxial crystal growth.

Herein the gallium arsenide substrate can inter alia be used for the production of semiconductor devices or electronic and optoelectronic devices, power components, high-frequency components, light-emitting diodes and lasers. The excellent surface properties of the substrate according to the invention enable the reproducible production of epitaxy layers with high yield.

A further aspect of the present invention relates to the use of an optical surface analyzer, preferably of an optical surface analyzer Candela CS20, for the optical contact-free quantitative characterization of the homogeneity of surface properties of gallium arsenide substrates by means of ellipsometric lateral substrate mapping, wherein even more preferably a laterally resolved measurement signal is corrected from a background having lower frequency by means of discrete complex Fourier transformation, preferably using the Levenberg-Marquardt algorithm.

EXAMPLES

Material and Methods

Candela ellipsometry: The surface properties of the substrate or respectively wafer (the properties of the oxide surface on the wafer) are characterized after the final cleaning with an optical surface analyzer (OSA). For the characterization of the homogeneity of the surface properties the phase shift measurement ("phase shift" channel) of the Candela CS20 from the company KLA-Tencor is used. The measurement principle and the measurement configuration have already been described above in connection with the ellipsometric lateral substrate mapping with an optical surface analyzer, to which reference is made herewith (see also FIG. 1). Because of the oblique incidence of the light the laser irradiates on the wafer an elliptical area with a dimension of approximately 5 µm in radial direction and approximately 4 µm in the direction perpendicular thereto. The fluctuations of the phase shift between the s component and the p component of the reflective laser beam from the measurement with the CS20 are used as a measure for the surface homogeneity of a GaAs wafer. In the mapping generated by the measurement local differences of these layer properties are represented as intensity differences.

In the measurement of GaAs surfaces furthermore a crystallographically caused, two-fold anisotropic reflection of the light occurs. The signal oscillation associated therewith is superimposed on the actual measurement signal. Typical results ("Candela maps") of ellipsometric lateral mappings of surfaces of differently produced and cleaned GaAs substrates are shown in FIG. 2. The different values of the phase shift are presented as light/dark contrast. In the background the typical two-fold light/dark variation stemming from the anisotropy of the light reflection at the GaAs itself can be discerned, wherein this variation varies comparatively slowly or respectively exhibits a comparatively low "frequency". In addition light and dark regions as well as stripe structures can be identified which are in contrast to the background signal and can be assigned to inhomogeneities or respectively defects. The intensity and the number of the deviations from the background characterize the homogeneity of a surface.

1. Candela Measurement

The parameters used for the Candela measurement are presented in Table 2 (shows the so-called "recipe parameters" of the measurement, "scan recipe") and Table 3 (shows the "wafer setup"). The parameters in the column "scan area" describe the wafer area scanned by the measurement and they are set in Table 3 exemplarily for the dimensions of a 150 mm wafer. The revolution speed of the measurement chuck is set with the parameter "speed". With the parameter "sampling average" a number of replication measurements can be defined from which the measurement result is determined. With the parameters "step size" the radial measurement resolution is set from which results the number of tracks in the parameter "total tracks". With the parameter "encoder multiplier" the azimuthal resolution is set. The setting "16×" corresponds to 16384 measurement points per track. The radial and azimuthal resolution given in the lower rows of the column "scan resolution" follows from the settings for "step size" and "encoder multiplier".

In the column "laser" the use of the azimuthal laser is predetermined which is required for the measurement of the phase shift as is the Q-polarization of the laser beam in the following column. In the last column of Table 2, finally in addition particular voltages and offsets are predetermined, which likewise to the other parameters have proven to be favorable for the measurements in the context of the present invention. When testing different settings for the radial resolution of the measurement, it was found that for a track distance between 10 and 75 µm there is no influence on the quantified measurement results for the surface homogeneity. The azimuthal resolution of 29 µm used for the measurements lies even in the outermost measurement circle over the used radial resolution of 50 µm.

TABLE 2

| Scan Area | Spindle control | Scan resolution | Laser | Q-Polarization | Gain and offsets Q-Polarization |
|---|---|---|---|---|---|
| Start: r = 75000 µm Angle = 0° | Speed = 3000 rpm | Step size = 50 µm | Circumferential | Phase | Sp1 = 0.5 V; Offset = 47 |
| Stop: r = 0 µm, Angle = 360° | Sampling average = 1 | Total tracks = 1501 | | | sp2 = 0.5 V; Offset = 56 |

TABLE 2-continued

| Scan Area | Spindle control | Scan resolution | Laser | Q-Polarization | Gain and offsets Q-Polarization |
|---|---|---|---|---|---|
| | | Encoder multiplier = 16× Total resolution: radial = 50.000 µm, Total resolution: angular = 0-28.762 µm | | | PMT circumf. = 400 V Auto PMT offset cir. = 0 Preset Gain Range |

In Table 3 still further parameters for the characterization of the GaAs wafers to be measured are summarized which relate to the wafer geometry, the wafer thickness (via the data set saved under "focus") as well as the general edge exclusion and a specific edge exclusion for the notch.

TABLE 3

| Wafer | Focus | Image angle | Analysis area | Image rotation angle |
|---|---|---|---|---|
| round 150 mm notch | L_6inGaAs 675 µm | As scanned | Start at 68000 µm radius Notch exclusion: l = 1500 µm, w = 3000 µm, Center = 0 und 270° | 0 |

As a result of the Candela measurement a data file is saved which besides basic information on the sample and the measurement conditions contains the measurement data together with the corresponding position coordinates in a binary packed format.

2. Background Correction

For the further improvement of the sensitivity of the method it is expedient to correct for or respectively to adjust for the two-fold intensity oscillations of the background caused by anisotropic reflection. For the spirally or respectively circularly recorded data tracks the two-fold profile is modeled by means of discrete complex Fourier transformation with appropriate frequencies using the Levenberg-Marquardt algorithm (see J. J. Moré) according to the following equation:

$$f(\varphi) = a_0 + a_2 \cos(4\pi\varphi + \alpha),$$

wherein $\varphi$ is the function variable, $\alpha$ is an angle offset, $a_0$ is the absolute offset and $a_2$ is the amplitude of the model function (see also FIG. 3). The background-corrected measurement signal of a data track is represented in FIG. 4. The background-corrected mappings now no more show two-fold symmetry (see FIG. 5) which could interfere with the characterization of deviations of the homogeneity of the surface properties.

3. Statistical Analysis of the Signal Variations

For the determination of the homogeneity of a substrate surface all signal variations from the ideal homogeneous surface (residuals of the background-corrected mappings) can be represented in a histogram (see FIG. 6). Since this distribution typically does not correspond to a Gaussian normal distribution, the frequently used standard deviation cannot be used as a measure of homogeneity. Rather appropriate percentiles need to be defined and computed. For the evaluation of the homogeneity of the GaAs surfaces the percentiles P1 or respectively quantiles $Q_{0.01}$ (see for example F. Schoonjans, D. De Bacquer, P. Schmid P, "Estimation of population percentiles", Epidemiology, 22, 2011, p. 750-751) were used for comparisons. Because of possible fluctuations of the excitation intensity the percentiles are normalized to the wafer average of the phase shift signal. In FIG. 7 the data are presented in a comparative manner. Herein box-and-whisker plots are used. The so far usual final cleaning technology produces wafers with surface homogeneities which exhibit 1% percentiles as defined above of less than −0.0065. Wafers produced according to the invention here show values of greater than −0.0065, preferably greater than −0.0060, more preferably greater than −0.0055, even more preferably greater than −0.0050, still more preferably greater than −0.0045, and values of greater than −0.0040, preferably greater than −0.0030, more preferably greater than −0.0020, in particular greater than −0.0010 and even up to 0.0000 can be taken into consideration.

4. Classification and Counting of Defects

The background-corrected mappings can also be characterized by means of defect classification of the analysis software of the Candela CS20. The mappings show light and dark regions as well as stripe structures which can be assigned to inhomogeneities or respectively defects. The intensity and the number of deviations from the background characterize the homogeneity of a surface. The intensity differences are classified and counted with respect to their strength and areal extension. Particular parameters are selected with which the signals to be analyzed and the defects to be analyzed are defined. For the definitions made in the present case see Table 1 as well as Tables 2-3. The negative and positive intensity fluctuations (deviations) are taken into account from a threshold value of 0.05%. The kernel length describes the averaging region, the kernel type denotes the kind of averaging. In case the positive and negative exceedances of the threshold values fulfill the distance criteria defined under "radial stitching" and "circular stitching" they are counted as individual defects and summed-up over the wafer. The stitching parameters in this regard specify the minimum distance of measurement points which positive or negative exceedances need to exhibit in order to be counted as separate defects. These defects are only counted if they are greater than 1000 µm$^2$. The sum of such defects is a measure for the homogeneity of a wafer (see FIG. 8). For wafers produced according to so far usual technology, based on a wafer or respectively substrate diameter of 150 mm as reference, defect numbers or >6000 or respectively defect areas of >2 cm$^2$ result. Wafers produced according to the invention show defect numbers of <6000, preferably <5000, more preferably <4000, even more preferably <3000, still more preferably <2000, still more preferably <1000, still more preferably <500, still more preferably <300, still more preferably <250, still more preferably <200, still more preferably <150 and particularly preferably <100 and/or defect areas of <2 cm$^2$, preferably less than 1 cm$^2$, more preferably less than 0.5 cm$^2$, even more preferably less than 0.1 cm², still more preferably less than 0.05 cm², still more preferably less than 0.01 cm², still more preferably less than 0.005 cm², and particularly preferably less than 0.0035 cm² (see FIG. 9).

5. Roughness Measurement

For the measurement of the roughness in the context of the present invention white light interferometry was used. In white light interferometry interference images are recorded with a camera, wherein the interference images result from the superposition of the light from the measurement object with the light reflected from a reference mirror. For a topography measurement the z position of the objective is adjusted in small steps and at each position an interference image is recorded. An image stack is obtained from which the height data are computed. By using a white light source with short coherence length, surfaces can be captured with very good height resolution as is known for interferometric measurement methods. For the measurements of the roughness in the context of this invention the apparatus NewView 5022S from the company Zygo was used. The measurements were performed with an apparatus with an objective with 20× magnification. The measuring field size was 180×130 μm. The given roughness $R_a$ is the difference between the maximum and minimum height value for the given measurement field size.

6. Determination of the Etching Abrasion

For the determination of the etching abrasion in between the dry oxidation and the wet cleaning according to the different embodiments of the present invention a chemically resistant adhesive tape was adhered to the front side of a GaAs wafer. After the cleaning process this particular adhesive tape was detached in a residue-free manner and the height of the formed step was measured by means of the white light interferometer according to the above-mentioned method at 5 points.

Comparative Example 1

A GaAs wafer after the last polishing step is subjected to a basic cleaning with a 0.5% NH₄OH solution and an acidic cleaning with a 5% HF solution for the removal of metallic contaminations. Subsequently the particle removal from the wafer surface is carried out by a brush scrubbing process. The cleaning procedure of the GaAs wafer is finished by a rinsing with deionized water and the drying by means of spin drying. After this conventional process for the surface cleaning of the GaAs wafer in the measurement of the surface homogeneity with the measurement apparatus Candela CS20 using the above-described recipes for the measurement and defect analysis, a variation of the laterally resolved background-corrected measurement signal is found whose distribution percentile of 1% normalized to the wafer average of the phase shift signal is less than −0.0065, as well as, based on a 150 mm GaAs wafer as reference size, a defect number of greater than 6000 and a total defect area of greater than 2 cm² on the surface is found (see FIGS. 6-9).

Comparative Example 2

Subsequent to a conventional cleaning and drying as described in the first Comparative Example, a GaAs wafer is subjected to an oxidation process. The oxidation is carried out by irradiating the whole area of the wafer surface by means of short wavelength UV light (wavelength 220-480 nm, power 20-40 mW/cm²), while slowly rotating the wafer, for e.g. one minute. Subsequently the wafer is subjected in a process rack to a basic cleaning in a 0.5% NH₃ solution under the influence of megasound, it is subsequently rinsed in the overflow and then removed from the process rack and dried by means of spin drying at 2500 rpm. The measurement of the surface defects on thus cleaned substrates with the measurement apparatus Candela CS20 leads to a variation of the laterally resolved background-corrected measurement signal whose distribution percentile of 1% normalized to the wafer average of the phase shift signal is less than −0.0065, to more than 6000 individual defects and a total defect area of greater than 2 cm² on the surface of the 150 mm wafer as reference (see FIGS. 6-9).

Example 1

After the conventional cleaning procedure as in Comparative Example 1, a GaAs wafer is subjected to the further steps of dry oxidation, NH₄OH cleaning and DI water rinsing as in the Comparative Example 2. In contrast to the Comparative Example 2, however the wafer is not dried by means of spin drying, but according to the Marangoni process. The measurement of the surface defects with the measurement apparatus Candela CS20 gives a variation of the laterally resolved background-corrected measurement signal whose distribution percentile of 1% normalized to the wafer average of the phase shift signal is greater than −0.0065. Furthermore, less than 100 individual defects and a total defect area of less than 2 cm² have resulted on the GaAs surface of the 150 mm wafer, and thereby the superiority of this cleaning process compared to the conventional cleaning in Comparative Example 1 and even compared to an improved cleaning but with conventional drying in Comparative Example 2 is shown (see FIGS. 6-9).

Example 2

The cleaning of a GaAs wafer is initially carried out in a conventional manner as in the Comparative Example 2. Subsequently a dry oxidation and a basic cleaning with subsequent DI water rinsing are carried out as in the Comparative Example 2 or respectively in Example 1. Subsequent to the rinsing with DI water in this embodiment of the present invention a further acidic cleaning step in combination with ozone dissolved in the liquid is carried out. In the rinsing with DI water subsequent to the acidic cleaning step furthermore the addition of an acid or base is carried out in order to advantageously prevent the formation of an inhomogeneous oxide layer during the rinsing. Using 0.2% HCl and 50 ppm ozone in the acidic cleaning step over a process time of 3 minutes and using the subsequent DI water rinsing with addition of a small amount of 25% NH₃ solution, the measurement of the surface homogeneity with the measurement apparatus Candela CS20 carried out subsequently to the Marangoni drying leads to a variation of the laterally resolved background-corrected measurement signal whose distribution percentile of 1% normalized to the wafer average of the phase shift signal is greater than −0.0065. Furthermore, less than 100 defects and a total defect area of less than 2 cm² on the surface of the 150 mm GaAs wafer are found (see FIGS. 6-9).

In case the last DI water rinsing is performed without the addition of a pH value modifying substance, the defect level measured after the cleaning process can increase to above 2000 defects on a 150 mm GaAs wafer.

Example 3

When in the treatment according to Example 2 instead of ozone hydrogen peroxide is used as oxidizing agent in the acidic cleaning step, the Candela measurement after the Marangoni drying gives above 4000 defects.

The invention claimed is:

1. A process for producing a surface-treated gallium arsenide substrate, the process comprising the following sequence of steps:
   a) oxidation treatment of at least one surface of a gallium arsenide substrate in dry condition by means of UV radiation and/or ozone gas;
   b-i) contacting the at least one surface of the gallium arsenide substrate with an alkaline aqueous solution;
   b-ii) contacting the at least one surface of the gallium arsenide substrate with water;
   b-iii) contacting the at least one surface of the gallium arsenide substrate with an acidic aqueous solution comprising ozone as an oxidizing agent, wherein the ozone concentration in the acidic aqueous solution is between 10 ppm and 100 ppm;
   b-iv) contacting the at least one surface of the gallium arsenide substrate with water, wherein the water at least initially contains a pH value modifying additive comprising NH3 in an amount to make the water sufficiently basic to remove oxides or prevent oxide formation on the at least one surface; and
   c) Marangoni drying of the gallium arsenide substrate.

2. The process according to claim 1, wherein the alkaline aqueous solution comprises a solution of $NH_3$ or organic amine in water.

3. The process according to claim 1, wherein the acidic aqueous solution is a solution of HCl or HF in water.

4. The process according to claim 1, wherein in step b) subsequent to step iv) further steps according to the steps i) and ii) are carried out.

5. A process for producing a plurality of surface-treated gallium arsenide substrates, wherein simultaneously a plurality of gallium arsenide substrates in the process according to claim 1 is subjected to the respective steps a)-c).

6. A gallium arsenide substrate which is produced according to the process according to claim 1.

7. A plurality of gallium arsenide substrates, which are produced according to the process according to claim 1 wherein variation from substrate to substrate of laterally resolved background-corrected measurement signal in ellipsometric lateral substrate mapping is substantially the same for all substrates in the plurality of substrates.

8. The process according to claim 1, wherein step i) further comprises applying megasound to the alkaline aqueous solution.

9. A process for the production of a component structure comprising: epitaxially depositing, on the surface-treated gallium arsenide substrate produced according to claim 1, mixed crystal stacks of variable elements, respectively selected from the group consisting of: Ga, In, As, P, Al, and N.

10. The process according to claim 1 wherein the $NH_3$ is in a concentration of between 0.01 percent and 0.2 percent by volume.

* * * * *